(12) United States Patent
Johner et al.

(10) Patent No.: US 8,251,959 B2
(45) Date of Patent: Aug. 28, 2012

(54) LEAF SPRING VALVE AND CONE MEMBRANE VALVE

(75) Inventors: Pascal Johner, Sugiez (CH); Jean-Noel Fehr, Neuenburg (CH); Michel Saint-Ghislain, Duedingen (CH); Hanspeter Niklaus, Riken (CH); Felix Fuchs, Altburon (CH)

(73) Assignee: Roche Diagnostics International AG, Steinhausen (CH)

( * ) Notice: Subject to any disclaimer, the term of this patent is extended or adjusted under 35 U.S.C. 154(b) by 0 days.

(21) Appl. No.: 12/704,086

(22) Filed: Feb. 11, 2010

(65) Prior Publication Data

US 2010/0204661 A1    Aug. 12, 2010

(30) Foreign Application Priority Data

Feb. 11, 2009  (EP) .................................. 09152621

(51) Int. Cl.
*A61M 5/00* (2006.01)
(52) U.S. Cl. ........................ 604/247; 604/246
(58) Field of Classification Search .......... 604/245–248, 604/250, 256
See application file for complete search history.

(56) References Cited

U.S. PATENT DOCUMENTS

| | | | | |
|---|---|---|---|---|
| 4,236,880 A | * | 12/1980 | Archibald | 417/478 |
| 5,482,438 A | * | 1/1996 | Anderson et al. | 417/44.1 |
| 6,142,979 A | | 11/2000 | McNally et al. | |

FOREIGN PATENT DOCUMENTS

| | | |
|---|---|---|
| DE | 199 51 669 A1 | 4/2001 |
| EP | 1 466 646 A1 | 10/2004 |
| EP | 2 218 476 A1 | 8/2010 |
| WO | 2005 037349 A2 | 4/2005 |

* cited by examiner

*Primary Examiner* — Kevin C. Sirmons
*Assistant Examiner* — Imani Hayman
(74) *Attorney, Agent, or Firm* — Dinsmore & Shohl LLP

(57) ABSTRACT

A delivery device and a method for administering a fluid from a fluid reservoir, wherein an unintended free flow of the fluid from the reservoir to a recipient is reliably prevented, are disclosed. The delivery device has a tank for the fluid; a fluid delivery device which delivers the fluid from the tank; a valve body providing an input hole and an output hole; and an infusion set in order to guide the fluid from the tank to a distal end of the delivery device. The delivery device further provides a shutter assembly which is or can be mounted to the valve body and prevents the fluid from flowing inside the infusion set when the fluid exhibits a pressure which is lower than a predefined pressure.

10 Claims, 7 Drawing Sheets

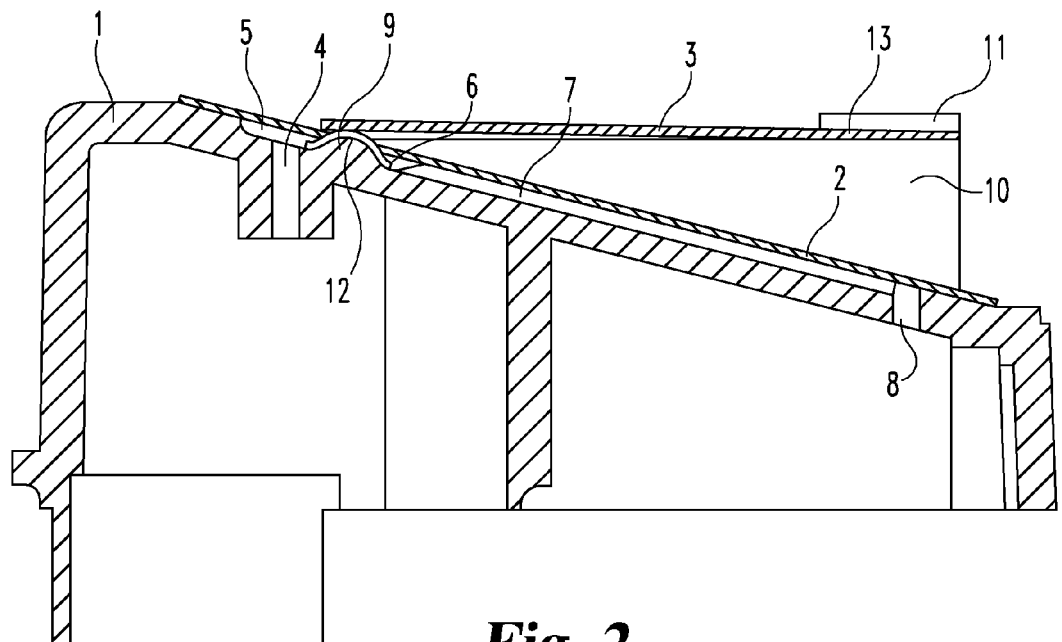
*Fig. 2*
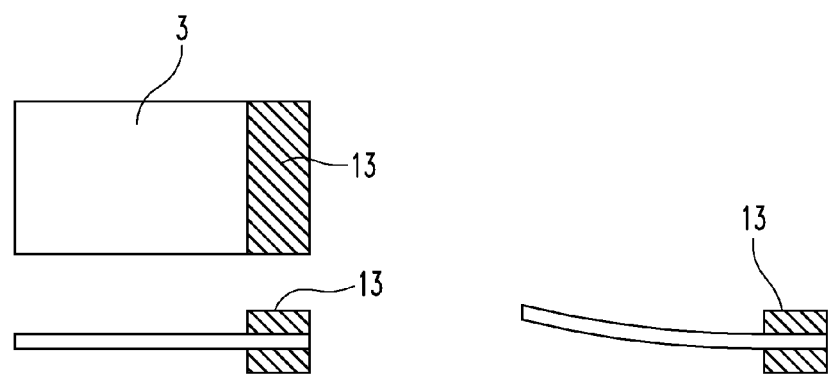
*Fig. 4a*  *Fig. 4b*

LEAF SPRING VALVE AND CONE MEMBRANE VALVE

TECHNICAL FIELD

Embodiments of the invention relate generally to a delivery device for a fluid, and in particular to a delivery device and a method for administering a fluid from a fluid reservoir, wherein an unintended free flow of the fluid from the reservoir to a recipient is reliably prevented.

BACKGROUND

Devices for administering a fluid drug in doses are known from the prior art. For example, U.S. Pat. No. 7,291,133 B1 describes a device comprising a container having a piston for administering a fluid drug through an outlet of the container, and a catheter which is connected to the outlet of the container and comprises a front end which faces away from the outlet and is connected to an injection needle. The device further comprises a valve which is positioned between the outlet and the injection needle in a flow cross section of the fluid drug and has an inlet end adjacent to the outlet and an outlet end adjacent to the injection needle. The valve allows the fluid drug to flow through the valve from the outlet to the injection needle when a fluid pressure exerted on the inlet end of the valve exceeds a pressure on the inlet end caused by the inherent weight of the fluid.

SUMMARY

In view of the above background, embodiments of the invention provide a delivery device and a method for administering a fluid, for example, a liquid fluid such as liquid insulin, from a fluid reservoir, wherein an unintended free flow of the fluid from the reservoir to a recipient is reliably prevented.

In one embodiment, a delivery device for a fluid is disclosed which comprises a tank for the fluid; a fluid delivery device which delivers the fluid from the tank; a valve body comprising an input hole and an output hole; an infusion set in order to guide the fluid from the tank to a distal end of the delivery device; and a shutter assembly provided to the valve body which prevents the fluid from flowing inside the infusion set when the fluid exhibits a pressure which is lower than a predefined pressure.

In another embodiment, a method for preventing a free flow of fluid in a delivery device having a valve body and a shutter assembly provided to the valve body is disclosed. The method comprises supplying the fluid from a tank to a collector chamber formed by the valve body and the shutter assembly situated inside or downstream of the tank; and using the shutter assembly to close off an outlet of the collector chamber and an inlet of a drain chamber correspondingly formed by the valve body and the shutter assembly by pressing at least one closing element onto a surface of a part of the valve body, which comprises the outlet of the collector chamber and the inlet of the drain chamber, with a predefined closing force. The method also comprises supplying additional fluid to the collector chamber until pressure inside the collector chamber exceeds a closing force of the shutter assembly such that the closing element lifts off the surface of the valve body and allows the fluid to flow from the outlet of the collector chamber to the inlet of the drain chamber.

These and other advantages and features of the invention disclosed herein will be made more apparent from the description, drawings and claims that follow.

BRIEF DESCRIPTION OF THE DRAWINGS

A detailed description of embodiments of the invention will be made with reference to the accompanying drawings, wherein like numerals designate corresponding parts in a several figures. The drawings show:

FIG. 2 is a cross-sectional side view of the assembled device of FIG. 1;

FIG. 4 is the leaf spring of the device of FIG. 1;

Figure 1:
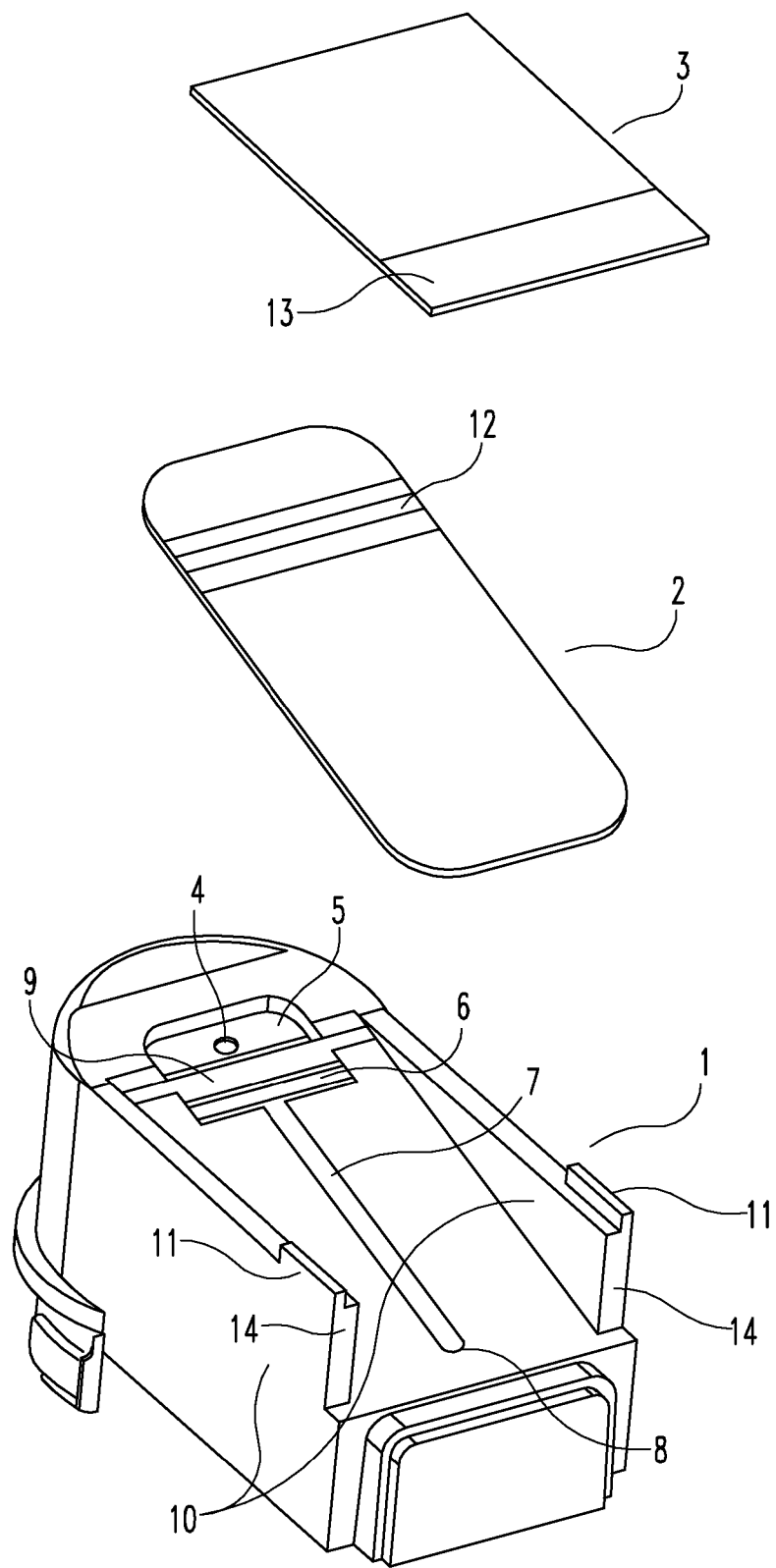
FIG. 1 is a perspective view of the disassembled parts of a first embodiment of the invention.

LIST OF REFERENCE SIGNS 1 valve body
2 strip
3 leaf spring
4 input hole
5 collector chamber
6 drain chamber
7 duct
8 output hole
9 boss
10 side wall
11 guide
12 strip fold
13 spring slice
50 adaptor housing
51 housing base
52 adaptor cover
53 valve body
55 aperture
56 aperture
58 output hole
59 gasket counter enclosure
60 gasket enclosure
61 manifold head
62 manifold head
63 input hole
64 duct
65 duct
66 cone
67 collector chamber
68 drain chamber
69 partition wall
70 membrane
71 rib
100 pump
110 tank
120 infusion set
130 recipient
200 pump 210 tank
220 infusion set
230 recipient
240 valve
300 spring force
400 input force
401 collector force
500 output force
501 drain force
700 spring force

DETAILED DESCRIPTION

Various embodiments of the invention relate to a delivery device for a fluid, which in one embodiment is a liquid fluid such as, for example, liquid insulin. In one embodiment, the delivery device comprises a reservoir for the fluid, a device for delivering the fluid from the reservoir, a valve body comprising an input hole and an output hole and an infusion set for guiding the fluid from the reservoir to a distal end of the delivery device. The delivery device further comprises a shutter assembly which is or can be mounted to the valve body and which prevents a free flow of fluid from the input hole to the output hole when the fluid exhibits a pressure which is lower than a predefined pressure. To this end, the fluid preferably does not flow inside the valve body but rather in the area of interaction between the valve body and the shutter assembly at the periphery of the valve body. This means that as long as the pressure of the fluid inside the delivery device is lower than a pressure which is in one embodiment defined by the design and/or material of the shutter assembly, the shutter assembly will stop the fluid from flowing to the distal end of the delivery device.

In one embodiment, the reservoir forms the proximal end of the delivery device, while the distal end can be an injection needle, a cannula, an injection jet nozzle or any other distal end of an injection set such as is known in the prior art. The reservoir can for example be a refillable container or an exchangeable container such as an ampoule. The device for delivering the fluid from the reservoir can be a pump, such as an electrical micro-pump or any other suitable pump such as is known in the prior art, or a piston which is connected to a piston rod and can be pushed manually or mechanically. The reservoir can advantageously be an integral part of the pump. The valve body in one embodiment is located between the reservoir and the infusion set and comprises an input hole and an output hole, but can also in principle be positioned at any other suitable position within the delivery device. The input hole of the valve body in one embodiment is in fluid communication with the outlet of the reservoir, while the output hole of the valve body in one embodiment is in fluid communication with a proximal end of the infusion set and thus with the recipient, which can for example be a patient's body if the fluid is a liquid medicine, for example, liquid insulin.

The shutter assembly is or can be mounted to the valve body. This means that the valve, which in its strictest sense is a free flow prevention valve, is provided as a unit comprising the valve body and the shutter assembly, which are fixedly connected to each other in such a way that they can only be separated from each other by destroying the valve. Alternatively, the valve body and the shutter assembly can be assembled in situ, and the connection can be such that the shutter assembly can be mounted to and dismounted from the valve body without being destroyed. Defective parts can then easily be exchanged, and the shutter assembly—which in one embodiment defines the opening force necessary to open the valve—can be exchanged if the delivery device is to be used in different applications which require different threshold pressures.

In one embodiment, the valve body and the shutter assembly or at least a part of it together form a collector chamber and a drain chamber of the valve. The collector chamber and the drain chamber each comprise an inlet and an outlet, wherein the inlet of the collector chamber is in fluid communication with the reservoir via the input hole of the valve body, and the outlet of the drain chamber is in fluid communication with the infusion set via the outlet hole of the valve body. The outlet of the collector chamber and the inlet of the drain chamber are both sealed off by the shutter assembly such that the fluid cannot pass from the collector chamber into the drain chamber unless the fluid exhibits a pressure which is greater than the sealing force of the shutter assembly as determined by its design and/or material.

The outlet of the collector chamber can exhibit the same size as the inlet of the drain chamber; however the size of the outlet of the collector chamber in one embodiment is greater than the size of the inlet of the drain chamber. Since the shutter assembly in one embodiment allows the fluid to flow from the collector chamber into the drain chamber and vice versa, different sizes of the respective inlet and outlet define different pressure values which have to be exceeded in order to open the free flow prevention valve. If the fluid flows from the reservoir into the infusion set, the pump pressure—i.e. the pressure generated by the action of the pump—will, in an ideal environment, be the same as the input pressure at the inlet of the collector chamber (the valve input) and the outlet of the drain chamber (the valve output). In reality, however, several external factors can act on the system which influence the input pressure and/or the output pressure, such factors being among others: a difference in height between the pump and the recipient; pressure variations between parts of the fluidic system (typically, the reservoir and the recipient), such as for example: changes in altitude (for example, a trip up a mountain or in a plane); environmental changes (for example, pressure and/or temperature); immersion of the pump or the recipient in a liquid; and elasticity of the components.

All these factors can lead to a differential pressure which is defined by the difference between the input pressure and the output pressure. It is the function of the free flow prevention valve to prevent an undesired flow of the fluid due to external factors, i.e. a flow not generated or controlled by the pump. A positive differential pressure, defined by the input pressure being greater than the output pressure, may lead to an uncontrolled free flow of the fluid from the reservoir to the recipient. A negative differential pressure, defined by the output pressure being greater than the input pressure, may lead to a reverse free flow of the fluid from the recipient to the reservoir.

To avoid an uncontrolled or reversed free flow, the shutter assembly must be designed such that the pump pressure is always greater than the maximum positive or negative differential pressure. Only then it is guaranteed that the flow of the fluid can always be controlled. In order to assure that the pump pressure always exceeds the actual differential pressure, it is necessary to determine the maximum differential pressure on the basis of the defined operating conditions of the pump, such as the temperature range, pressure range, length of the infusion set, etc., and on the basis of the design of the delivery system, i.e. the pump pressure must exceed the counter pressure of the shutter assembly plus the theoretical maximum differential pressure plus an additional safety value, in order to reliably rule out any free flow.

In various embodiments, the shutter assembly is tempered such that it exhibits a pressure force against the valve body and thus prevents a flow from the outlet of the collector chamber to the inlet of the drain chamber. If the fluid pressure exceeds the sealing force of the shutter assembly, the fluid pushes the shutter assembly away from the valve body, enabling the fluid to leave the collector chamber through the outlet of the collector chamber and to flow into the inlet of the drain chamber and subsequently through the outlet of the drain chamber and the output hole of the valve body, into the infusion set.

In one embodiment, the shutter assembly can be a spring valve which for example comprises at least the valve body, a strip and a leaf spring. This specific embodiment has the major advantage that it allows the opening and closing pressure to be adjusted in a simple way, by slightly adjusting the shape of the leaf spring. Alternative embodiments comprise a strip of ferromagnetic material and a magnet which is inserted in the valve body or, instead of a spring, an electromagnetic switch which is controlled by the pump. In one advantageous embodiment, the strip opening between the outlet of the collector chamber and the inlet of the drain chamber can be mechanically limited to a desired gap, thus providing the advantages of a constant gap opening and the absence of mechanical friction.

In another embodiment, the shutter assembly can be a membrane valve which comprises at least the valve body, an adaptor housing and a membrane. The membrane is made of an elastic material which has to be stretched in order to fit onto the adaptor housing, i.e. it has a tight fit on the adaptor housing and presses against the adaptor housing with a membrane pressure which is defined by the mechanical properties of the membrane material, the membrane thickness and its elongation due to being stretched on the adaptor housing. The adaptor housing can have any suitable shape or form. In an alternative embodiment, the membrane can be compressed in order to create a membrane force which acts against the adaptor housing when trying to expand back to its original size.

These valves can for example be advantageously used in combination with reservoirs, such as insulin reservoirs, which have no free flow prevention mechanism such as stopper friction or a stopper threaded connection. This includes the majority of commercially available reservoirs, for example reservoirs for injection pens. Due to their design, the free flow prevention valves according to the present invention can be manufactured to relatively large tolerances, without substantially influencing the opening and closing pressure.

The invention also comprises a method for preventing a free flow of fluid in a delivery device, wherein the fluid is pumped from a reservoir or tank and delivered to a collector chamber of a free flow prevention valve, where it is stopped by a shutter assembly which seals off the outlet of the collector chamber and the inlet of a drain chamber, and wherein a flow of the fluid from the collector chamber to the drain chamber can only be achieved by providing the fluid at a predefined pressure, at which the fluid opens the shutter assembly by pushing it away from the outlet of the collector chamber and the inlet of the drain chamber.

The invention will now be described on the basis of several illustrated embodiments of the figures. The illustrated embodiments are merely intended to explain in greater detail the advantages of the invention, without in any way limiting the content or scope of the invention.

FIG. 1 shows a perspective view of the disassembled parts of a first embodiment of a free flow prevention valve. The valve comprises a valve body 1, wherein the surface of the valve body 1 comprises notches which form canals or grooves forming a collector chamber 5, a drain chamber 6 and a duct 7 for the fluid to be guided through the valve, and comprises a boss 9. The valve body 1 further comprises an input hole 4 to allow fluid to enter the collector chamber 5, and an output hole 8 at a distal end of the duct 7. The valve in the example shown is horseshoe-shaped with a rounded end—referred to here as the distal end—comprising the input hole 4, and a straight end referred to here as the proximal end and comprising the output hole 8. The valve body 1 of the example shown has the shape of a wedge, with the horseshoe-shaped end being the thicker end. The side walls 10 of the valve body 1 run essentially parallel to each other and exhibit a constant height. The ends of the side walls comprise vertical faces 14 and, at the most proximal end, integrally formed guides 11 which project from the upper side of the side walls 10 and have a smaller wall thickness than the side walls 10.

The valve further comprises a strip 2 which is essentially rectangular in shape, but with rounded corners. The strip 2 comprises a strip fold 12. The strip is designed to fit onto the surface of the wedge-shaped part of the valve body 1 in such a way that the strip fold 12 rests on the boss 9. In one embodiment, the strip 2 comprises one layer and exhibits an equal thickness throughout. However, the thickness of the strip at or adjacent to the strip fold 12 can vary, either by design or due to bending. The strip 2 can also be made of different materials, i.e. can be composed of more than one layer and/or can comprise adjacent sections made of different materials.

Lastly, the valve comprises a leaf spring 3 with a spring slice 13, wherein the leaf spring 3 is designed to rest on the side walls 10 of the valve body 1 and the spring slice 13 is designed to rest between the guides 11.

FIG. 2 shows a cross-sectional side view of the assembled free flow prevention valve comprising the valve body 1, the strip 2 and the leaf spring 3. The strip 2 rests tightly on the valve body 1 and covers the collector chamber 5, the drain chamber 6 and the duct 7. The distal end spring slice 13 of the leaf spring 3 rests on the side walls 10 where the guides 11 are formed, and the proximal end of the leaf spring 3 rests on the strip fold 12, which in turn rests on the boss 9. Since the top of the boss 9—with the strip 2 resting on it—protrudes beyond the side walls 10, and since the leaf spring 3 is fixedly held by the guides 11 at its distal end forming the spring slice 13, the leaf spring 3 is bent away from the surface of the valve body 1, thus creating a force which presses the strip fold 12 onto the boss 9.

It will be clear from FIGS. 1 and 2 that a fluid which enters the collector chamber 5 through the input hole 4 cannot flow into the drain chamber 6 and subsequently into the duct 7 and out through the output hole 8, unless the pressure provided by the fluid and acting on the strip 2 is greater than the pressure of the leaf spring 3 which presses the strip fold 12 onto the boss 9. It will also be clear that the free flow prevention valve is designed to allow a flow from the inlet hole 4 to the output hole 8 and vice versa.

In order to ensure that no fluid can bypass the chambers 5, 6 and the duct 7, the strip 2 in one embodiment is fixedly connected to the surface of the valve body such that the strip 2 can only be pressed away from the valve body 1 in a region covering the outlet of the collecting chamber 5, the strip fold 12 and the inlet of the drain chamber 6, over a width (from side wall 10 to side wall 10) which is essentially equal to the width of the two chambers 5, 6.

The valve body 1 of the example embodiment is divided into a proximal part, designed to be connected for example to a reservoir or pump, and a distal part, designed to be connected for example to an infusion set or drainage line. The shutter assembly described could for example be used to ensure that a liquid medicine, for example liquid insulin, is only injected into the body of a patient when a pump supplies the insulin at a pressure which is greater than the pressure generated by the leaf spring 3, taking into consideration other environmental effects such as changes in altitude, environmental changes, immersion of the pump and/or the patient's body in a liquid, etc.

Figure 3:
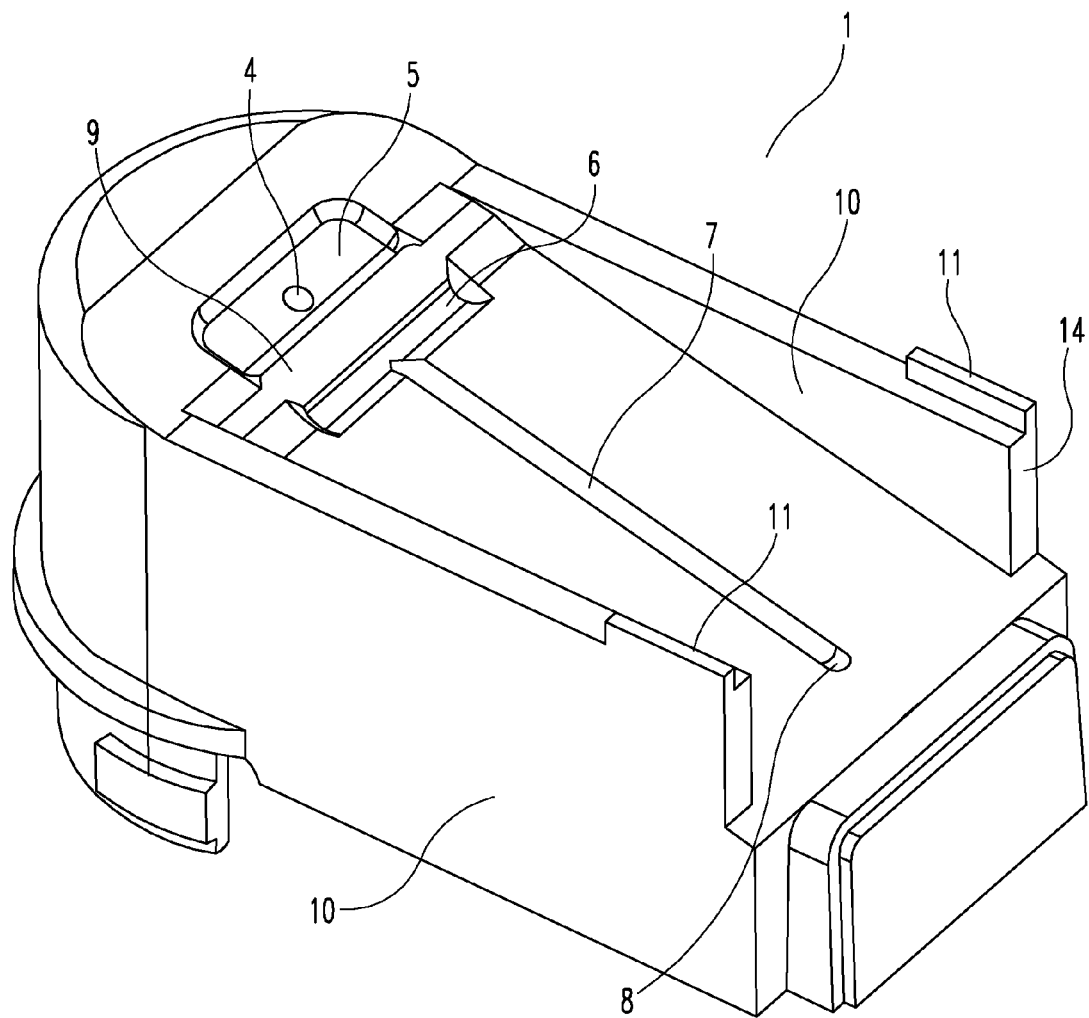
FIG. 3 is the valve body of the device of FIG. 1, in an enlarged representation.

FIG. 3 is an enlarged perspective view of the valve body 1, showing in greater detail the parallel side walls 10, the integrally formed guides 11, the inlet hole 4, the outlet hole 8, the collecting chamber 5, the drain chamber 6, the duct 7 and the boss 9. It should be emphasised that the valve body 1 is only an example. In accordance with the present invention, the valve body can have any form suitable to its specific application; the chambers 5, 6, the duct 7 and the boss 9 can be formed as appropriate; and the output hole 8 can also for example be situated in the drain chamber 6. In short, there are many possible design variations, without departing from the scope of the invention.

FIG. 4 shows one possible embodiment of the leaf spring 3, showing the spring slice 13 in a view from above and in two lateral views, one lateral view showing the leaf spring 3 before the free flow prevention valve (not shown) is assembled and the other showing the leaf spring 3 after it has been installed on the valve body.

Figure 5A:
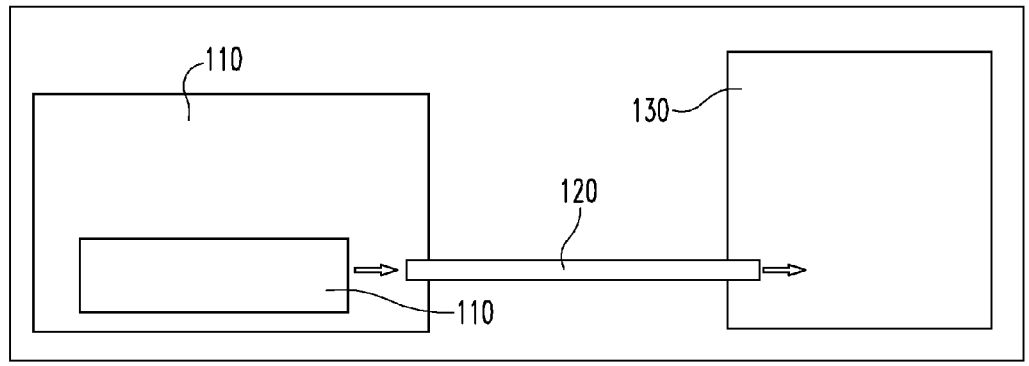
FIG. 5 shows two fluidic systems.
Figure 5B:
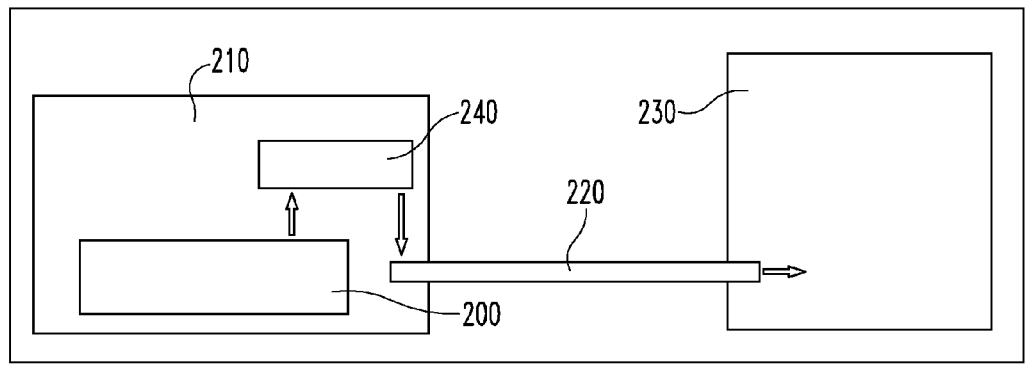

FIGS. 5*a* and 5*b* are schematic diagrams of a fluidic system. FIG. 5*a* shows a fluidic system without the valve of the present invention, comprising a pump 100 and a tank 110 for a liquid medicine, such as insulin, which is integrated into the pump 100. The pump 100 delivers the liquid to an infusion set 120, which guides the liquid to a recipient 130, for example a syringe or a patient's body.

FIG. 5*b* shows a fluidic system incorporating the valve of the present invention. In the fluidic system of FIG. 5*b*, the pump 200 delivers the liquid from the tank 210, through a valve 240 which is formed in accordance with the present invention, to the infusion set 220 and subsequently to the recipient 230.

It should again be emphasised that the flow paths indicated by the arrows in FIGS. 5*a* and 5*b* are merely examples. The tank 110, 210 need not be an integral part of the pump 100, 200, and the valve 240 need not be positioned on the threshold between the tank 110, 210 or pump 100, 200 and the infusion set 120, 220.

Figure 6:
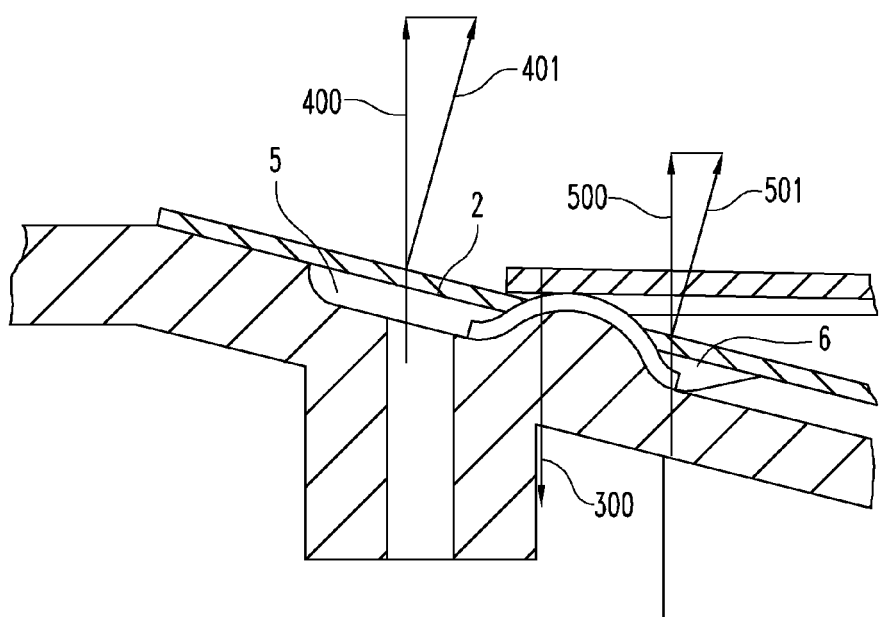
FIG. 6 is a diagram showing the forces acting in the device of FIG. 2.

FIG. 6 is a diagram showing the forces which act on the strip 2. As can be seen, the spring force 300 acts in a first direction, while the input force 400 and the output force 500 act in the opposite direction. Since the collector chamber 5 and the drain chamber 6 are positioned in an inclined plane, the force actually acting on the strip 2 is the resultant collector force 401 and/or resultant drain force 501, respectively. It will be clear that the collector force 401 must exceed the spring force 300 in order for the free flow prevention valve to open and allow the liquid to flow from the collector chamber 5 into the drain chamber 6.

Figure 7:
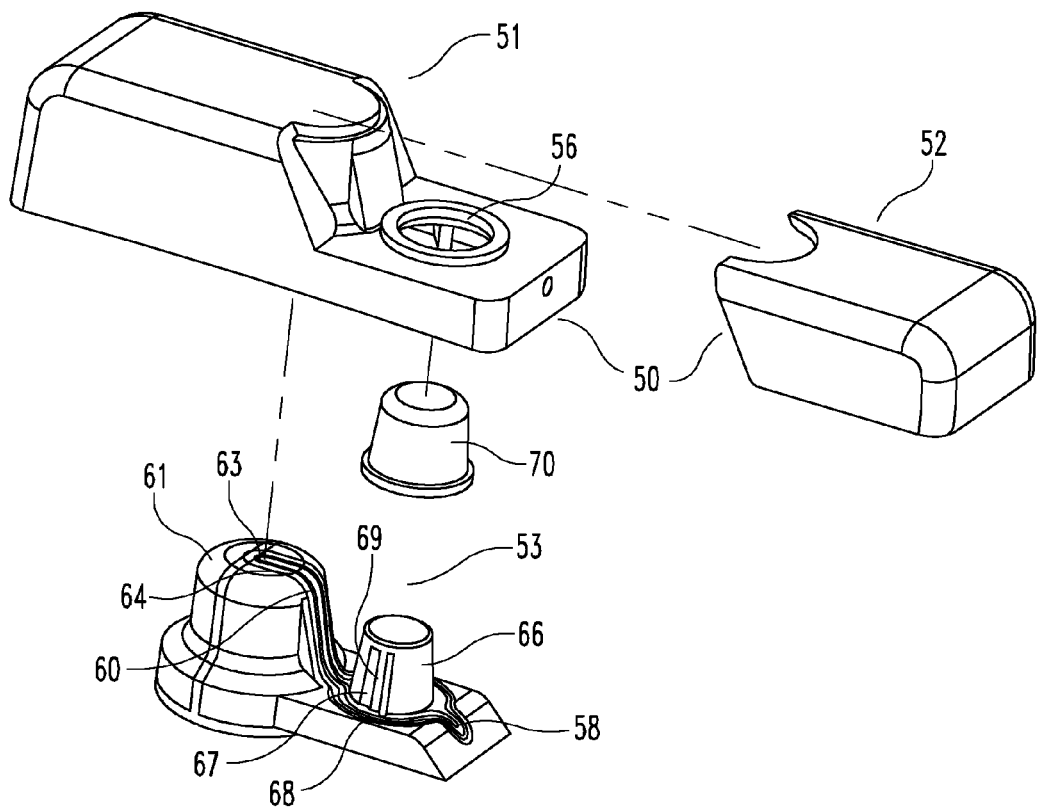
FIG. 7 is a perspective view of the disassembled parts of a second embodiment of the invention.

FIG. 7 shows a perspective view of the disassembled parts of a second embodiment of a free flow prevention valve. The valve comprises an adaptor housing 50 comprising an adaptor housing base 51 and an adaptor cover 52, wherein the adaptor cover 52 can be attached to the adaptor housing base 51, to form the adaptor housing 50. The adaptor housing base 51 comprises a first part having a closed surface, and a second part having an aperture 56. The valve body 53 of the second example embodiment comprises two parts, namely a manifold head 61 and a cone 66, wherein the cone 66 comprises two slit-shaped grooves forming a collector chamber 67 and a drain chamber 68, respectively, and is designed to fit through the aperture 56. A partition wall 69 separates the collector chamber 67 from the drain chamber 68. The manifold head 61 further comprises an input hole 63, while the end of the valve body 53 adjacent to the aperture 56 comprises an output hole 58. Ducts 64, 65 are formed on the surface of the valve body 53, in order to guide the liquid from the input hole 63 to the collector chamber 67 and from the drain chamber 68 to the output hole 58. The duct structures are surrounded by a gasket enclosure 60 such that no liquid can leak from the ducts 64, 65.

The valve further comprises an elastic membrane 70 which exhibits a form similar to the form of the cone 66, but with an inner diameter which is slightly smaller than the outer diameter of the cone 66. The membrane 70 therefore has to be stretched in order to fit onto the cone 66. Once mounted on the cone 66, the membrane 70 will try to return to its non-stretched state, due to its elasticity. This results in a tight encapsulation of the cone 66 by the membrane 70.

Figure 8:
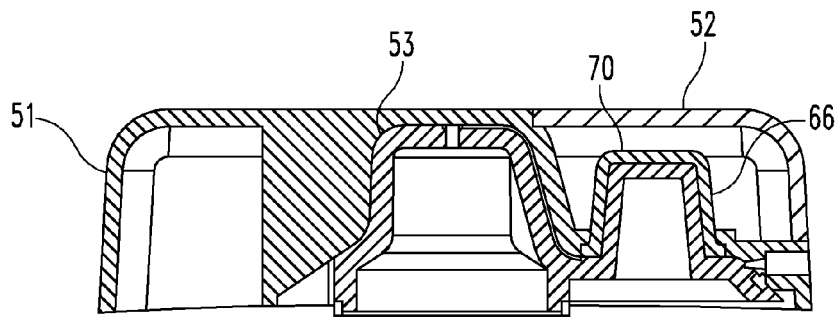
FIG. 8 is a cross-sectional side view of the assembled device of FIG. 7.

As can best be seen in FIG. 8, which is a cross-sectional side view of the assembled free flow prevention valve, the membrane 70 is positioned on the cone 66 first, before the valve body 53 is inserted into the housing base 51 from below, such that the cone 66 and the membrane 70 are positioned in the aperture 56.

Figure 9A:
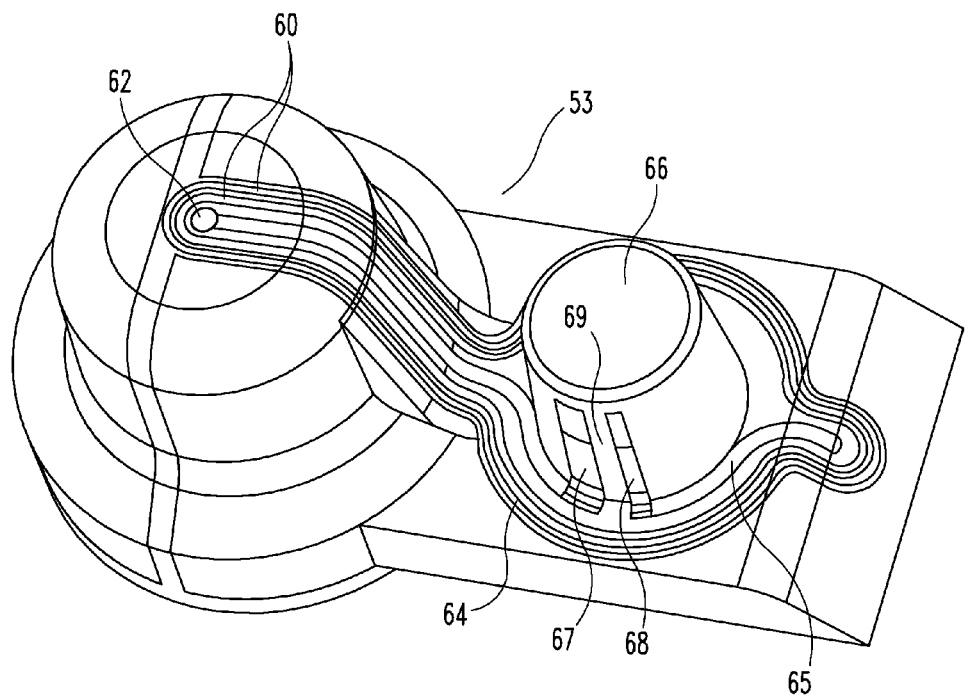
FIG. 9a is a perspective view of the housing base of the device of FIG. 7 from above.
Figure 9B:
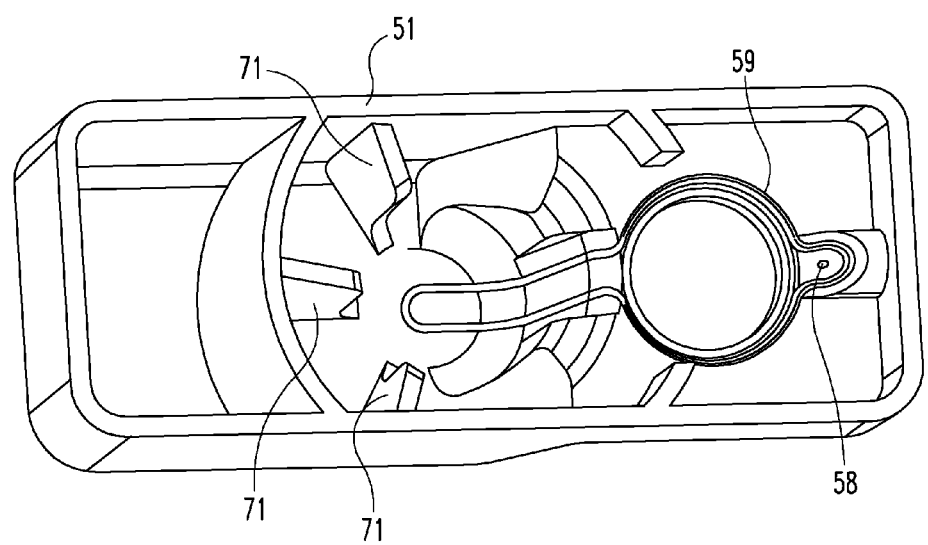
FIG. 9b is a perspective view of the housing base of the device of FIG. 7 from below.

FIG. 9*a* is a perspective view of the housing base 51 from above, showing the aperture 56 and the output hole 58 which in an assembled free flow prevention valve of the second embodiment is in fluid communication with the output duct 65 (not shown). FIG. 9*b* is a perspective view of the housing base 51 from below. Inside the housing base 51, positioning ribs 71 are formed in order to guide the valve body 53, together with the stretched membrane 70, into position. Gasket counter enclosures 59, which together with the gasket enclosures 60 form a gasket for the liquid flowing in the ducts 64, 65 from the input hole 63 to the collector chamber 67 and from the drain chamber 68 to the output hole 58, are inserted into or formed together with the valve body 53.

Figure 10:
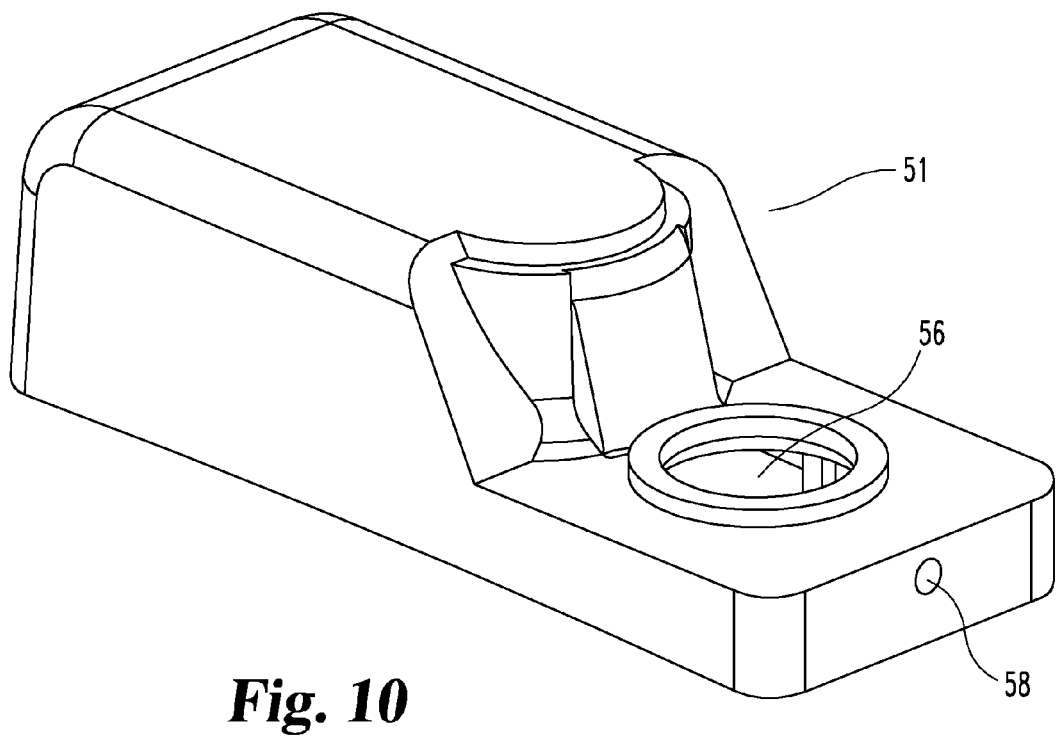
FIG. 10 is the valve body of the device of FIG. 7, in an enlarged representation.

FIG. 10 is an enlarged representation of the valve body 53, showing the manifold head 62 comprising the input hole 63 and the input duct 64, the cone 66 comprising the collector chamber 67, the drain chamber 68, the partition wall 69 between the collector chamber 67 and the drain chamber 68, the drain duct 65 and the output hole 58.

Having described the disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure. As such, the embodiments described above are purely illustrative and not meant to limit the scope of the invention.

What is claimed is:

1. A delivery device for a fluid comprising:
a tank for the fluid;
a fluid delivery device which delivers the fluid from the tank;
a valve body comprising an input hole and an output hole;
an infusion set in order to guide the fluid from the tank to a distal end of the delivery device; and
a spring valve comprising the valve body, a strip having a strip fold, and a leaf spring having a spring slice that presses the strip against the valve body, wherein the spring valve prevents the fluid from flowing inside the infusion set when the fluid exhibits a pressure which is lower than a predefined pressure.

2. The delivery device according to claim 1, wherein the valve body comprises a collector chamber providing the input hole and a drain chamber providing the output hole, and wherein the leaf spring that presses on the strip provides the force to be overcome in order to open the flow connection between the outlet of the collector chamber and the inlet of the drain chamber.

3. The delivery device according to claim 2, wherein the strip rests tightly on the valve body and covers the collector chamber, the drain chamber and a duct.

4. The delivery device according to claim 1, wherein a distal end of the leaf spring rests on side walls where guides are formed, and a proximal end of the leaf spring presses the strip against a boss formed on the valve body.

5. The delivery device according to claim 4, wherein the boss extends beyond the side walls of the valve body.

6. The delivery device according to claim 5, wherein the side walls of the valve body run parallel to each other and exhibit a constant height such that the ends of the side walls comprise vertical faces with integrally formed guides that project from the upper side of the side walls having a smaller wall thickness than the side walls.

7. The delivery device according to claim 1, wherein the valve body has an incline plane relative to the leaf spring.

8. The delivery device according to claim 1, wherein a distal end of the leaf spring rests on side walls where guides are formed above the output hole of the valve body and a proximal end of the leaf spring rests on the strip comprising a strip fold adjacent the input hole of the valve body.

9. The delivery device according to claim 1, wherein the leaf spring that presses on the strip provides a spring force in a first direction, and both an input force and an output force in a second direction that is opposite to the first direction.

10. The delivery device according to claim 1, wherein the valve body further comprises a collector chamber and a drain chamber, and wherein the leaf spring that presses on the strip results in a collector force, wherein the collector force must exceed the spring force in order to open the flow connection from the collector chamber and into the drain chamber.

* * * * *

UNITED STATES PATENT AND TRADEMARK OFFICE
CERTIFICATE OF CORRECTION

| | | |
|---|---|---|
| PATENT NO. | : 8,251,959 B2 | Page 1 of 1 |
| APPLICATION NO. | : 12/704086 | |
| DATED | : August 28, 2012 | |
| INVENTOR(S) | : Pascal Johner et al. | |

It is certified that error appears in the above-identified patent and that said Letters Patent is hereby corrected as shown below:

Col. 10, Lines 9-10, Claim 8, "strip comprising a strip fold adjacent" should read -- strip adjacent --.

Signed and Sealed this
Twenty-third Day of October, 2012

David J. Kappos
*Director of the United States Patent and Trademark Office*